United States Patent [19]
Baba

[11] 4,442,842
[45] Apr. 17, 1984

[54] ULTRASONIC SCANNER FOR EXAMINATION OF A COELIAC CAVITY

[76] Inventor: Kazuo Baba, 1079, Kitano-machi, Hachioji-shi, Tokyo, Japan

[21] Appl. No.: 203,511

[22] Filed: Nov. 3, 1980

[30] Foreign Application Priority Data

Nov. 12, 1979 [JP] Japan ................. 54-146240

[51] Int. Cl.³ ............................. A61B 10/00
[52] U.S. Cl. .................... 128/660; 128/6; 73/620
[58] Field of Search ............ 128/660, 663, 4, 6; 310/348, 354; 73/620-623

[56] References Cited
U.S. PATENT DOCUMENTS

| | | | |
|---|---|---|---|
| 3,779,234 | 12/1973 | Eggleton et al. | 128/660 |
| 3,827,115 | 8/1974 | Bom | 128/660 |
| 4,008,603 | 2/1977 | Paulissen | 73/623 X |
| 4,029,084 | 6/1977 | Soldner | 128/660 |
| 4,084,582 | 4/1978 | Nigam | |
| 4,149,419 | 4/1979 | Connell et al. | 128/660 X |
| 4,208,602 | 6/1980 | Stoller | 73/620 X |
| 4,249,539 | 2/1981 | Vikomerson et al. | 128/660 |
| 4,274,421 | 6/1981 | Dory | 128/660 |
| 4,330,874 | 5/1982 | Sorwick | 73/620 X |

FOREIGN PATENT DOCUMENTS

| | | |
|---|---|---|
| 67 | 6/1978 | European Pat. Off. . |
| 54-1984 | 1/1979 | Japan . |
| 387698 | 9/1973 | U.S.S.R. ............... 128/660 |

OTHER PUBLICATIONS

Hisanaga, K. et al., Proceed. of the 23rd Annual Meeting of the Aium, 1978, p. 108.
Taylor et al., Ultrasound in Med. & Biol., vol. 5, No. 2-A, 1979, pp. 129-138.

*Primary Examiner*—Lee S. Cohen
*Assistant Examiner*—John C. Hanley

[57] ABSTRACT

With an ultrasonic scanner for coeliac examination, the distal end of the insertion section is provided with a distal end part consisting of a beam-scanning section and beam transmitting and receiving section. The beam-scanning section comprises a beam mirror set in a beam-scanning chamber formed in a casing. A reflection plane formed at one end of the beam mirror is inclined at an angle of, for example, 45° to its rotation axis. The beam mirror is rotated by means of a mirror shaft and flexible shaft. The beam transmitting and receiving section comprises a holder in which a vibrator is set. The holder is securely fitted into a receptacle formed in the casing by the threaded engagement of a fitting cap with the receptacle. The vibrator is electrically connected to the insertion body in a detachable state.

12 Claims, 4 Drawing Figures

ULTRASONIC SCANNER FOR EXAMINATION OF A COELIAC CAVITY

BACKGROUND OF THE INVENTION

This invention relates to an ultrasonic scanner for coeliac examination which is inserted into the coeliac cavity of an examinee to inspect the physiological condition of the organs of the coeliac cavity.

With the conventional endoscope comprising an integrally formed ultrasonic scanner for coeliac examination, the control section is inseparably coupled to a narrow insertion section to be introduced into the coeliac cavity. The insertion section comprises a bendable body and a distal end part integrally formed with the distal end of the bendable body. The distal end part comprises a section for transmitting and receiving ultrasonic beams (hereinafter referred to as "beam transceiver") and beam-scanning section actuated in response to an output signal from the beam transceiver. The beam transceiver has a function of emitting beams in a predetermined direction and receiving echoes sent back in a predetermined direction. The beam-scanning section has a function of scanning a predetermined region of the coeliac cavity by ultrasonic beams emitted from the beam transceiver and transmitting the reflected echoes of the ultrasonic beams to the beam transceiver.

With the ultrasonic scanner for coeliac examination arranged as described above, the beam transceiver and beam-scanning section are integrally formed with the insertion section and cannot be removed therefrom. Therefore the prior art ultrasonic scanner has the drawback that where the coeliac cavity is diagnosed from various angles of observation by applying ultrasonic beams having different properties, then it is necessary to provide several kinds of beam scanner in accordance with not only the different angles of observation but also other different characteristics of ultrasonic beams (e.g. frequency, focal length, etc.).

It is accordingly the object of this invention to provide an ultrasonic scanner for coeliac examination which allows for the free exchange of a desired component.

SUMMARY OF THE INVENTION

To attain the above-mentioned object, this invention provides an ultrasonic scanner for coeliac examination which comprises an insertion section introduced into a coeliac cavity of a human body, a beam transceiver for emitting ultrasonic beams and receiving reflected echoes thereof and a beam-scanning section for scanning a predetermined region of the coeliac cavity by ultrasonic beams generated from the beam transceiver and sending the echoes of the ultrasonic beams back to the beam transceiver, and wherein at least two of the above-mentioned insertion section, beam transceiver and beam scanner are detachably fitted to each other.

DETAILED DESCRIPTION

Figure 1:
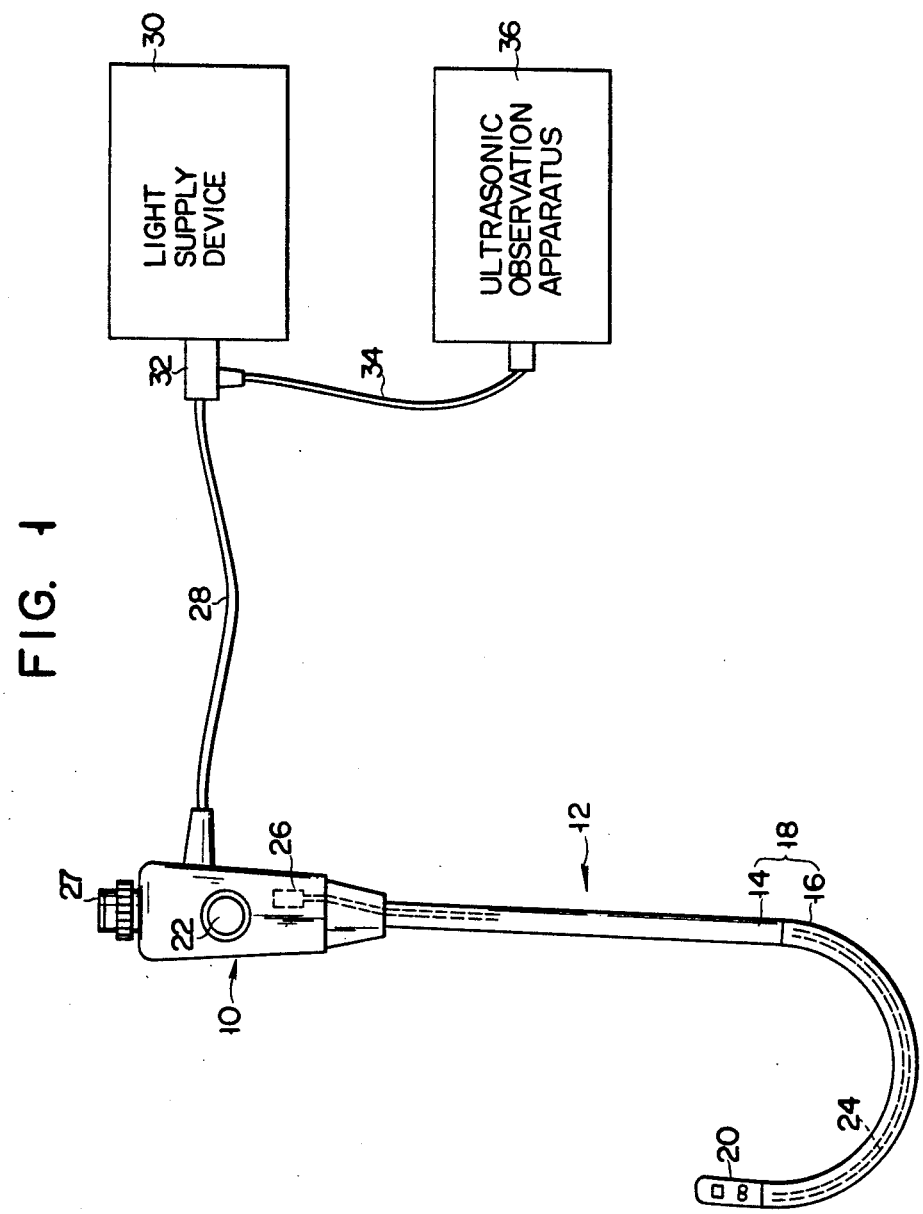
FIG. 1 shows the arrangement of the whole of a diagnosing device provided with an ultrasonic scanner according to one embodiment of this invention.

With an ultrasonic scanner of FIG. 1 according to one embodiment of this invention, an insertion section 12 is connected to a control section 10. The insertion section 12 comprises an insertion body 18 consisting of a narrow cylindrical flexible tube 14 and a bendable tube 16, and a distal end part 20 fitted to the free distal end of the bendable tube 16. The bendable tube 16 can be freely bent by remote control from a control knob 22 mounted on the control section 10, enabling the distal end part 20 to be applied in a direction adjustable according to the operator's desire. A flexible shaft 24 extends through the later described passage of the insertion section 12. The flexible shaft 24 is connected at one end to a power source 26 provided in the control section 10, and at the other end to the later described mirror shaft. The control section 10 further comprises an eyepiece 27 through which the coeliac cavity of an examinee is observed and a universal cord 28 provided at least with an optical fiber bundle through which an illumination light sent forth from a light supply device 30 is conducted to the coeliac cavity. Received in the universal cord 28 is the later described signal line extending from the distal end part 20. The signal line is connected to an ultrasonic observation apparatus 36 through an external signal cord 34 extending outward from a connector 32 fitted to the universal cord 28. The ultrasonic observation apparatus 36 comprises, for example, the known high frequency pulse generator, waveform detector, signal amplifier and display (such as a cathode-ray tube) (none of these members are shown).

Figure 2:
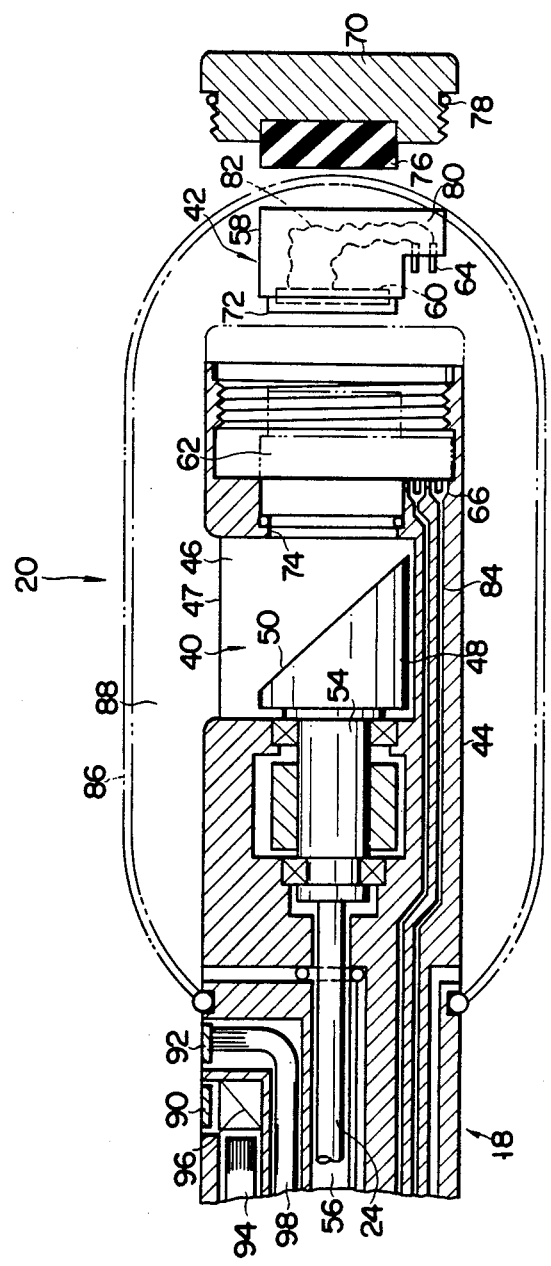
FIG. 2 is an enlarged sectional view of the distal end part of the ultrasonic scanner of FIG. 1.

Referring to FIG. 2 indicating the distal end part 20 in enlargement, the distal end part 20 comprises a beam-scanning section 40 and beam transceiver 42. The beam-scanning section 40 comprises a beam-scanning chamber 46 open to one lateral side of a substantially cylindrical casing 44 and a beam mirror 48 set in the beam-scanning chamber 46. The beam-scanning chamber 46 has an opening 47. The beam mirror 48 is formed of a round columnar body whose end face constitutes a reflection plane 50 inclined at an angle of substantially 45° to its rotation axis. The beam mirror 48 is fitted to a concentric mirror shaft 54 of the cylindrical casing 44, and is rotated with the mirror shaft 54 connected to the flexible shaft 24 extending through the passage 56 of the insertion body 18.

The beam transceiver 42 comprises a substantially round cylindrical holder 58, one end of which is fitted with a vibrator (i.e., a transducer) 60 facing the reflection plane 50 of the beam mirror 48. The beam transceiver 42 is set in the receptacle 62 of the casing 44, such that the center of the vibrator 60 is aligned with the rotation axis of the beam mirror 48. The contact pins 64 of the beam transceiver 42 are fitted into pin sockets 66 formed in the inner wall of the casing 44 for electric connection. The beam transceiver 42 is fixed in the receptacle 62 by a keep cap 70 threadedly engaged with the receptacle 62. A vibrator cover 72 securely supporting the vibrator 60 is inserted into a supporting hole 74 formed in the receptacle 62, and pressed against the inner wall of the receptacle 62 by means of an elastic element 76 fitted to the inner wall of the keep cap 70. Therefore, the beam transceiver 42 is securely fixed in the receptacle 62 of the casing 44. A water proofing ring 78 is tightly attached to the outer peripheral wall of the keep cap 70. The contact pins 64 of the beam transceiver 42 are mounted on a projection 80 extending outward from the peripheral wall of the cylindrical holder 58. The contact pins 64 are electrically connected to the vibrator 60 by means of a first signal line 82. Pin sockets 66 corresponding to the contact pins 64 are formed in the end face of the casing 44 of the beam-scanning section 40. The pin sockets 66 are connected to the control section 10 through two second signal lines 84 laid in the inner wall of the casing 44, and then to the ultrasonic observation apparatus 36 shown in FIG. 1. Where the beam transceiver 42 is fitted into the casing 44, then the contact pins 64 are inserted into the pin sockets 66, causing the vibrator 60 of the beam transceiver 42 to be electrically connected to the beam-scanning section 40.

The distal end part 20 arranged as described above is enclosed in a balloon (formed of plastic material) 86 which is filled with a beam-guiding medium 88. An observation window 90 and illumination window 92 are formed in that lateral wall of the insertion body 18 which lies close to the distal end part 20. The observation window 90 is optically connected to the eyepiece 27 (FIG. 1) of the control section 10 by means of a prism 96 and an image guide 94 which is formed of an optical fiber bundle and extends from the control section 10 to the insertion body 18. The illumination window 92 is optically connected to the light supply device 30 by means of a light guide 98 which is formed of an optical fiber bundle and extends through the insertion body 18 and universal cord 28 (FIG. 1). A light emitted from the light supply device 30 is conducted to the illumination window 92 through the light guide 98 of the universal cord 28 to shed a light on the coeliac cavity.

Where an ultrasonic scanner embodying this invention which is arranged as described above is applied in effecting the ultrasonic beam diagnosis of any of the organs disposed in the depth of the coeliac cavity of a human body, for example, the stomach, then the insertion section 12 is introduced into the stomach. The bendable tube 16 is properly bent by the actuation of the control knob 22 of the control section 10, causing the distal end part 20 to be located at a prescribed part of the stomach. The opening 47 of the beam-scanning chamber 46 of the distal end part 20 is directed to the affected part of the stomach which is to be examined. At this time, the balloon 86 is directly pressed against the affected wall of the stomach. Where the tight attachment of the balloon 86 to the stomach wall is ascertained, then a high frequency pulse generator (not shown) is operated, causing pulsated ultrasonic beams to be irradiated from the vibrator 60. When striking against the reflection plane 50 of the beam mirror 48, the pulsated ultrasonic beams are reflected from the beam mirror 48 at right angles to propagate into the tissue of the stomach wall through the opening 47. When the stomach wall includes an affected tissue which indicates an abnormal condition, the ultrasonic beams propagated into the tissue of the human body are reflected from the boundary surface of the abnormal affected tissue. The reflected echoes are again brought back to the reflection plane 50 of the beam mirror 48 through the opening 47. At this time, the echoes are reflected from the beam mirror 48 toward the vibrator 60 at right angles. The echoes carried to the vibrator 60 are converted into the corresponding signals by the vibrator 60. The converted signals are transmitted to the external ultrasonic observation apparatus 36 (FIG. 1) through the signal lines 82, 84. Later, the converted signals are collectively displayed in the form of a planigram.

With an ultrasonic scanner of FIG. 1 according to one embodiment of this invention, the beam transceiver 42 is detachably fitted to the beam-scanning section 40, enabling the operator to easily replace the beam transceiver by a separate similar member having a different property. At this replacement, the keep cap 70 is first removed from the receptacle 62 to take out the beam transceiver 42 therefrom. Next, another desired beam transceiver is fitted into the receptacle 62. Thereafter, the keep cap 70 is threadedly engaged with the receptacle 62. Since the beam transceiver can be easily exchanged, it is unnecessary to provide various kinds of ultrasonic scanner, even where selection is made of, for example, the frequency characteristic of the vibrator or a focal length of ultrasonic beams in accordance with the condition in which the physiological aspect of the coeliac cavity is diagnosed. In other words, provision of a single beam scanner and a plurality of beam transceivers enables a variety of coeliac diagnoses to be carried out efficiently and at low cost.

Figure 3:
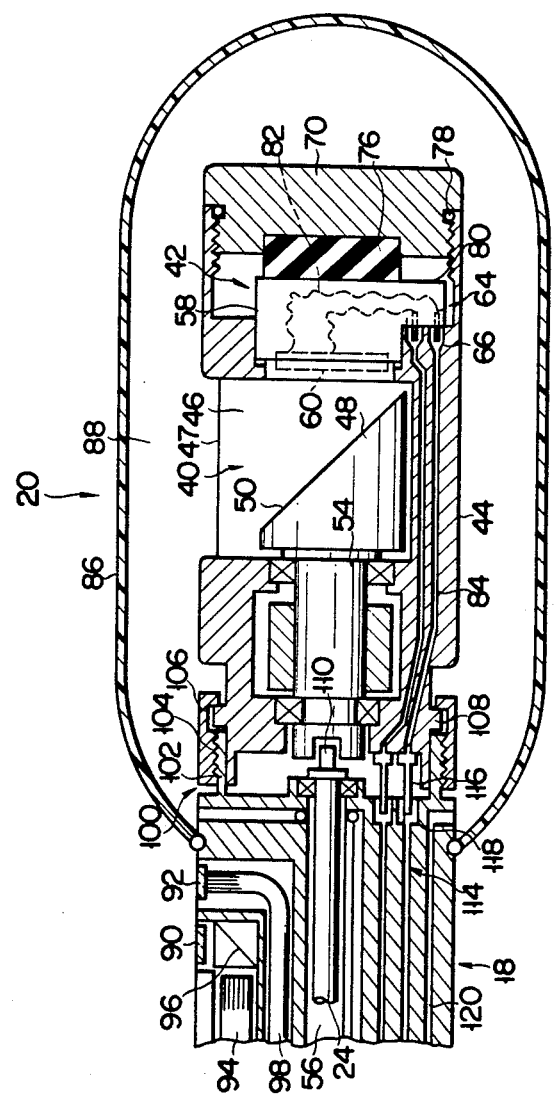
FIG. 3 is an enlarged sectional view of the distal end part of an ultrasonic scanner according to another embodiment of the invention.
Figure 4:
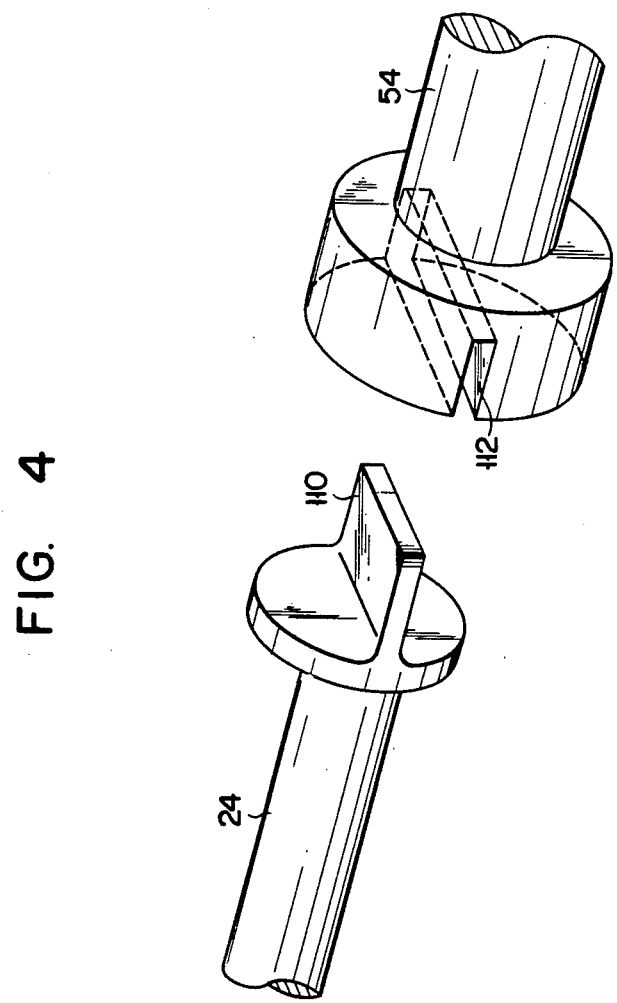
FIG. 4 is an exploded oblique view of a mirror shaft and flexible shaft to be joined together to constitute an ultrasonic scanner.

Description is now given of an ultrasonic scanner of FIG. 3 according to another embodiment of this invention. With this embodiment, the beam-scanning section 40 fitted with the beam transceiver 42 is made detachable from the insertion body 18. In other words, the beam-scanning section 40 is detachably fitted to the insertion body 18 by means of mechanical coupling means 100. This mechanical coupling means 100 comprises a connection tube 102 integrally projecting from the distal end of the insertion body 18. External threads 104 are formed on the outer peripheral surface of the connection tube 102. A box nut 106 engageable with the connection tube 102 is provided on the outer periphery of the free end of the casing 44 of the beam-scanning section 40. The inner wall of the box nut 106 is provided with internal threads corresponding to the external threads 104 of the connection tube 102. The rear end of the box nut 106 is engaged with a flange 108 of the casing 44. This flange 108 causes the box nut 106 to be fitted to the distal end of the casing 44 in such a manner that the box nut 106 can be rotated in the circumferential direction of its own, but can not be moved in the axial direction of its own. As shown in enlargement in FIG. 4, the distal end of the flexible shaft 24 comprises an integrally formed plate-shaped projection 110 having a predetermined thickness. The distal end face of the mirror shaft 54 is provided with a groove 112 into which the plate-shaped projection 110 can be inserted. Where the projection 110 of the flexible shaft 24 is inserted into the groove 112 of the mirror shaft 54, to effect connection between both members 24, 54, then the rotation of the flexible shaft 24 is transmitted to the mirror shaft 54. The above-mentioned arrangement enables the distal end part 20 consisting of the beam-scanning section 40 and beam transceiver 42 to be detachably fitted to the insertion body 18. In this case, the distal end part 20 is electrically connected to the insertion body 18 by electric connection means 114. This electric connection means 114 comprises two contact pins 116 projectively provided at the rear end of the casing 44 for connection to two second signal lines 84. Two pin sockets 118 corresponding to the two contact pins 116 are formed in the free distal end face of the insertion body 18. The pin sockets 118 are connected to two third signal lines 120, which in turn are respectively connected to the universal cord 28 and external signal code 34 (both shown in FIG. 1) which extend outward from the control section 10 (FIG. 1). Where the distal end part 20 is fitted to the insertion body 18 by the mechanical coupling means 100, then the signal lines 84 extending from the vibrator 60 are electrically connected to the third signal lines 120 extending through the insertion body 18 by means of the contact pins 116 and pin sockets 118. The second embodiment of FIG. 3 is constructed in the same way as that of the first embodiment of FIG. 1 in other respects than described above, description thereof being omitted.

With the second embodiment of FIG. 3, the beam transceiver 42 is detachably fitted to the beam-scanning section 40, which is also detachably fitted to the insertion body 18. Therefore, not only the beam transceiver 42, but also the beam-scanning section 40 are made freely and easily exchangeable with similar members having different properties. For instance, where an already fitted beam mirror 48 is replaced by another beam mirror whose reflection plane is inclined at a different angle from that of above-mentioned already used beam mirror, then the box nut 106 is first disengaged from the external threads 104. Then the distal end part 20 is separated from the insertion body 18. Another distal end part fitted with a separate beam mirror whose reflection plane has a freshly required angle of inclination is attached to the insertion body 18. The box nut 106 is again threadedly engaged with the connection tube 102. Where, therefore, it is necessary to diagnose any of the organs of a human body by carrying out beam scanning at a selected angle, it is unnecessary to provide a large variety of beam scanners. A new distal end part of a desired type has only to be provided. Therefore, an ultrasonic scanner embodying this invention can be operated at a far lower cost than has been possible in the past.

Although the present invention has been shown and described with respect to particular embodiments, nevertheless, various changes and modifications which are obvious to a person skilled in the art to which the invention pertains are deemed to lie within the spirit, scope and contemplation of the invention. With the ultrasonic scanner of FIG. 3 according to the second embodiment of this invention, the beam transceiver 42 is detachably fitted to the beam-scanning section 40 as in the first embodiment of FIG. 1. However, this arrangement is not always required. In other words, the beam transceiver 42 and beam-scanning section 40 may be integrally formed. Further, the mechanical connection applied in the foregoing embodiments can be effected not only by threaded engagement but also simply by insertion.

What is claimed is:

1. In an endoscope apparatus, an ultrasonic scanner for internal examination, comprising:
   a flexible endoscope insertion body which is sized for introduction into a cavity of a living body such as a human body and having an end;
   ultrasonic beam-scanning means, provided at said end of said insertion body to be introduced into said body cavity, and including scanning means for scanning a selected region of said body cavity with ultrasonic beams and guiding reflected echoes of said ultrasonic beams in a predetermined direction with respect to said insertion body, said beam-scanning means including a casing member carrying said scanning means having a transducer-receiving hollow receptacle at an end portion thereof and in the path of said guided reflected echoes, said transducer-receiving receptacle having an opening for receiving a transducer therein, said scanning means and said transducer-receiving receptacle being arranged adjacent each other in the axial direction of said endoscope insertion body;
   ultrasonic transducer means mounted in said transducer-receiving receptacle of said casing member and having a predetermined conversion property, for (i) converting into an ultrasonic beam to be supplied to said beam-scanning means a high frequency electrical pulse which is transmitted to said transducer means through said insertion body and said casing member in accordance with said predetermined conversion property and (ii) converting said reflected echoes into a corresponding electrical signal for transmission to an external component through said casing member and said insertion body in accordance with said predetermined property, said transducer means being removably disposed in said transducer-receiving receptacle of said casing member, whereby said transducer means may be replaced with another transducer means having a different property, when so desired;
   said casing member comprising a cap removably closing said opening of said transducer-receiving receptacle to retain a transducer means in said receptacle; and
   an elastic element interposed between said cap and a transducer means received in said transducer-receiving receptacle to elastically press said transducer means into said receptacle.

2. Apparatus according to claim 1, further comprising lead wire means having an end portion extending into said transducer-receiving receptacle to engage said transducer means, and another portion extending through said insertion section and said casing member for carrying said high freguency pulse and said electrical signal.

3. Apparatus according to claim 2, wherein said transducer means includes:
   a transducer element having said conversion property;
   holder means having a shape corresponding to said transducer-receiving receptacle and being removably receivable in said receptacle, said transducer element being secured to said holder means.

4. Apparatus according to claim 2, wherein said casing member is detachably connected to said end of said endoscope insertion body, so that said beam-scanning means may be replaced with another beam-scanning means which has a casing member mechanically interchangeable with said first-mentioned casing member and a different scanning property.

5. Apparatus according to claim 4, wherein said lead wire means includes a first lead wire section which is substantially contained endoscope in said insertion body and which has an end section disposed at said end of said endoscope insertion body, and a second lead wire section which is substantially contained in said casing member and which has an end section disposed so as to be electrically connected to said end section of said first lead wire section when said casing member is attached to said endoscope insertion body.

6. Apparatus according to claim 5, further comprising:
   light supply means for emitting light to illuminate said body cavity; and
   light transmitting means coupled to said light supply means and to said endoscope insertion body for guiding said light into said body cavity through said endoscope insertion body and for transmitting reflected light from said body cavity to a predetermined region when said endoscope insertion body, said beam-scanning means and said transducer means are introduced into said body cavity.

7. Apparatus according to claim 4, wherein said beam-scanning means includes a chamber in said casing member and a rotatable mirror member received in said chamber of said casing member, said chamber having an opening on one side thereof, said mirror member being rotatable about an axis, and said mirror member comprising a round columnar body having an end face which constitutes a reflection plane inclined to the rotation axis thereof, whereby the ultrasonic beam from said transducer means is reflected by said reflection plane and transmitted from said chamber through said opening of said chamber, and said reflected echoes are transmitted to said transducer means through said opening of said chamber by said reflection plane.

8. Apparatus according to claim 7, which further comprises a flexible shaft member extending through said endoscope insertion body and said casing member for transmitting rotational torque to said mirror member.

9. Apparatus according to claim 8, wherein said flexible shaft member comprises a first shaft section having a free end connected to said mirror member and contained substantially in said casing member, and a flexible second shaft section contained substantially in said insertion body, said second shaft section having an end adapted to be mechanically and detachably connected to said free end of said first shaft section, said mirror member receiving said rotational torque through said first and second shaft sections when said casing member is attached to said insertion body.

10. Apparatus according to claim 1, wherein said transducer-receiving receptacle of said casing member includes a concavity at an end portion of said casing member in which a transducer means is received.

11. Apparatus according to claim 1 or 2, wherein said transducer-receiving receptacle of said casing member comprises a threaded portion adjacent the opening thereof, and wherein said cap comprises threads thereon for threadably engaging said threaded portion of said transducer-receiving receptacle.

12. Apparatus according to claim 1 or 2, wherein said elastic element is secured to a portion of said cap which faces said opening of said transducer-receiving receptacle.

* * * * *

UNITED STATES PATENT AND TRADEMARK OFFICE
CERTIFICATE OF CORRECTION

PATENT NO. : 4,442,842
DATED : April 17, 1984
INVENTOR(S) : Kazuo BABA

It is certified that error appears in the above-identified patent and that said Letters Patent is hereby corrected as shown below:

COLUMN 6 (claim 5), line 64, change "endoscope in said insertion body" to --in said endoscope insertion body--.

Signed and Sealed this

Nineteenth Day of February 1985

[SEAL]

Attest:

DONALD J. QUIGG

Attesting Officer

Acting Commissioner of Patents and Trademarks

UNITED STATES PATENT AND TRADEMARK OFFICE
CERTIFICATE OF CORRECTION

PATENT NO. : 4,442,842
DATED     : April 17, 1984
INVENTOR(S) : Kazuo BABA

It is certified that error appears in the above-identified patent and that said Letters Patent is hereby corrected as shown below:

On the title page, insert the name of the Assignee as follows:

--[73] Assignee: OLYMPUS OPTICAL CO., LTD.
                 Tokyo, Japan--.

Signed and Sealed this

Eleventh Day of June 1985

[SEAL]

Attest:

DONALD J. QUIGG

Attesting Officer    Acting Commissioner of Patents and Trademarks